United States Patent
Sasse

[11] Patent Number: 5,715,065
[45] Date of Patent: Feb. 3, 1998

[54] METHOD AND DEVICE FOR DETERMINATION OF THE ALBEDO OF A PARTICLE OF RANDOM FORM

[75] Inventor: Christian Sasse, Winnenden, Germany

[73] Assignee: Deutsche Forschungsanstalt fuer Luft- und Raumfahrt e.V., Bonn, Germany

[21] Appl. No.: 639,376

[22] Filed: Apr. 26, 1996

[30] Foreign Application Priority Data

Apr. 28, 1995 [DE] Germany .................. 195 15 659.5
Mar. 16, 1996 [DE] Germany .................. 196 10 439.4

[51] Int. Cl.⁶ .................. G01N 21/55; G01J 1/04
[52] U.S. Cl. .................. 356/446; 356/236
[58] Field of Search .................. 356/433, 446, 356/236; 250/228

[56] References Cited

U.S. PATENT DOCUMENTS 4,575,252  3/1986  Akiyama .................. 356/236

FOREIGN PATENT DOCUMENTS 22 04 079   8/1973  Germany .
33 16 170  11/1983  Germany .
36 05 436  11/1986  Germany .
2171607     3/1990  Japan .................. 356/236

*Primary Examiner*—Frank G. Font
*Assistant Examiner*—Amanda Merlino
*Attorney, Agent, or Firm*—Barry R. Lipsitz; Ralph F. Hoppin

[57] ABSTRACT

In order to provide a method and device for determination of the albedo or light absorption of a particle of random form, it is proposed that a particle is electrostatically charged and is positioned contact-free in an Ulbricht sphere by means of an electric field; that the particle thus positioned is illuminated with a measuring light beam passing through the Ulbricht sphere with defined intensity, defined beam cross-section and defined intensity distribution over this; that the intensity of the solely particle-based diffuse radiation in the Ulbricht sphere is measured by means of a sensor; that the cross-sectional area of the particle illuminated by the measuring light beam is determined; that the intensity of the solely reference particle-based diffuse radiation is measured in the same manner with a reference particle with known albedo; and that the albedo of the particle is determined from the ratio of the intensities of the particle-based and reference particle-based diffuse radiation taking into account the cross-sectional area of the particle illuminated by the measuring light beam and the cross-sectional area of the reference particle.

27 Claims, 3 Drawing Sheets

METHOD AND DEVICE FOR DETERMINATION OF THE ALBEDO OF A PARTICLE OF RANDOM FORM

BACKGROUND OF THE INVENTION

The invention relates to a method for determination of the albedo or light absorption of a particle of random form, wherein the light absorption amounts to (1-Albedo).

No method is known thus far to enable determination of the degree of albedo and emittance of a single particle of random form with a size to which the laws of geometric optics apply.

Computational methods are only possible when the refractive index is known and the particle has an ideal spherical, cylindrical or ellipsoidal form.

However, these computational methods fail in the case of particles with an irregular, i.e. random, form.

The importance of the albedo and emittance of a particle is, for example, of significance to the dye industry in the production of pigments or for the determination of emittance in industrial furnaces.

Therefore the object of the invention is to provide a method and a device for determination of the albedo of a particle of random form.

SUMMARY OF THE INVENTION

This object is achieved with a method of the above-described type in that a particle is electrostatically charged and is positioned contact-free in an Ulbricht sphere by means of an electric field; that the particle thus positioned is illuminated with a measuring light beam passing through the Ulbricht sphere with defined intensity, defined beam cross-section and defined intensity distribution over this; that the intensity of the solely particle-based diffuse radiation in the Ulbricht sphere is measured by means of a sensor; that the cross-sectional area of the particle illuminated by the measuring light beam is determined; that the intensity of the solely reference particle-based diffuse radiation is measured in the same manner with a reference particle with known albedo; and that the albedo of the particle is determined from the ratio of the intensities of the particle-based and reference particle-based diffuse radiation taking into account the cross-sectional area of the particle illuminated by the measuring light beam and the cross-sectional area of the reference particle.

Hence, the measurement method according to the invention provides the possibility of determining the albedo of particles of random form and, working from the albedo, also the emittance of this particle of random form.

In this case, the determination of the cross-sectional area of the particle illuminated by the measuring light beam can occur before or after or simultaneously with the measurement of the intensity of the particle-based diffuse radiation in the Ulbricht sphere.

Moreover, the particle is preferably positioned close to the centre point of the Ulbricht sphere for measurement of the intensity of the particle-based diffuse radiation.

Purely on principle, it would be conceivable within the scope of the solution according to the invention to position the particle and the reference particle contact-free in the Ulbricht sphere respectively by means of a d.c. electric field. However, a particularly advantageous solution provides that the particle and the reference particle are each positioned contact-free respectively by means of an a.c. electric field, in which case the a.c. electric field is superimposed on the d.c. electric field and the combination of both results in a minimum potential for the electrostatically charged particle.

In this case, the minimum potential preferably lies close to the centre point of the Ulbricht sphere.

For the solution according to the invention, the intensity and intensity distribution of the measuring light beam may be determined, for example, with a standard intensity measuring device. However, so as to be able to take into account the effect of the Ulbricht sphere directly, it has proved particularly advantageous if the intensity of the measuring light beam is determined after transillumination of the Ulbricht sphere without illumination of the particle and measurement of the intensity. With this, all the effects of the Ulbricht sphere and also of the electrodes arranged therein for the generation of the electric field are already taken into account on measurement of the intensity of the measuring light beam.

Determination of the intensity of the measuring light beam may already be achieved, for example, at a time point at which no particle has yet been positioned contact-free in the electric field.

However, it is particularly advantageous if determination of the intensity of the measuring light beam by illumination into the Ulbricht sphere is already achieved at a time point at which the particle or the reference particle is already positioned in the electric field in the Ulbricht sphere. For this purpose, the particle or reference particle is then preferably positioned next to the measuring light beam, which is possible by adjusting the d.c. electric field or a.c. electric field.

Measurement is particularly precise if the relative positions of the measuring light beam and the Ulbricht sphere to one another remain unchanged for determination of the intensity of the measuring light beam and for determination of the intensity of the diffuse particle-based radiation in the Ulbricht sphere.

This may be achieved in a particularly simple manner if firstly the particle is positioned next to the measuring light beam for determination of the intensity of the measuring light beam and then only needs to be moved into the measuring light beam for determination of the intensity of the diffuse particle-based radiation.

So as to be able to carry out an exact determination of the albedo of the particle, it is preferably provided that the intensity distribution of the measuring light beam is determined in each point of the cross-sectional area of the beam thereof.

An alternative solution to this provides that a measuring light beam with an essentially Gaussian intensity distribution over its cross-sectional area is used, and therefore only determination of the cross-sectional area of the beam is still required.

No further details have thus far been given with respect to the cross-sectional area of the particle illuminated by the measuring light beam. Hence, an advantageous embodiment provides that the cross-sectional area of the particle illuminated by the measuring light beam is determined by projection of a shadow outline of the particle positioned in the measuring light beam in the direction of propagation of the measuring light beam onto a projection surface.

This may be achieved in a particularly simple manner if the projection surface is arranged outside the Ulbricht sphere.

Since the particles are generally very small, it is particularly advantageous if the shadow outline of the particle is projected on the projection surface as an image magnified by an optical projection unit, so that the shadow outline of the particle is more clearly visible.

In this case, it would be possible, for example, to directly observe the shadow outline on the projection surface.

However, it is more advantageous if the projection surface is formed by a surface of a photosensitive storage element, and in the simplest case this storage element can be a standard photographic film.

However, it is even more advantageous if the projection surface is formed by the surface of an electronic image logging unit, since the shadow outline can be stored and evaluated substantially more advantageously with this electronic image logging unit.

In order to achieve a very high degree of precision in the evaluation of the cross-sectional area of the particle illuminated by the measuring light beam, it is advantageously provided that for measurement of the cross-sectional area of the particle illuminated by the measuring light beam, the measuring light beam and the particle stand in the same relative position to one another as during measurement of the intensity of the diffuse particle-influenced radiation in the Ulbricht sphere.

Purely theoretically, it would be conceivable to also determine the cross-sectional area of the particle when it is partially illuminated and carry out the measurement of the diffuse particle-based radiation to determine the albedo therefrom. However, it is particularly advantageous if for measurement of the intensity of the diffuse particle-based radiation in the Ulbricht sphere with an illuminated particle, the particle is positioned as a whole within the beam cross-section of the measuring light beam so that the entire cross-sectional area of the particle is illuminated in a plane perpendicular to the propagation of the measuring light beam.

Moreover, this procedure also facilitates the determination of the cross-sectional area of the particle illuminated by the measuring light beam by projection of the shadow outline onto the projection surface.

No further details have thus far been given in association with the previous explanation of the individual embodiments with respect to the size and determination of the cross-sectional area of the reference particle. Hence, it is possible, for example, with a reference particle to already work with such a reference particle with known cross-sectional area.

However, it is particularly advantageous if determination of the cross-sectional area of the reference particle is achieved in the same manner as that of the cross-sectional area of the particle, so that further calibration of the method according to the invention is possible, for example, through the cross-sectional area of the reference particle.

It has additionally proved advantageous if the illumination of the cross-sectional area of the reference particle is determined in the same manner as in the case of the cross-sectional area of the particle to thus ensure that in the method according to the invention, only the part of the cross-sectional area of the reference particle which is illuminated by the measuring light beam is included in the determination of the albedo. It is particularly advantageous in this case if the particle and the reference particle are positioned in the same cross-sectional region of the measuring light beam so that determination of the albedo can be carried out with the same intensity ratios, in particular in the case of intensity distribution with irregular cross-section.

In addition, the invention relates to a device for determination of the albedo or light absorption of particles of random form, which is characterised according to the invention in that the device has an electrode arrangement for the contact-free positioning of an electrostatically charged particle; that the electrode arrangement is surrounded by an Ulbricht sphere; that the Ulbricht sphere is fitted with a sensor for measurement of the diffusely reflected radiation in the Ulbricht sphere; and that the Ulbricht sphere has an entrance port for a measuring light beam for illumination of the particle held contact-free by the electrode arrangement.

The advantage of the device according to the invention is that it provides the possibility, on the one hand, of positioning the particle in the measuring light beam and to detect the particle-influenced diffusely reflected radiation within the Ulbricht sphere, and from this intensity of the particle-influenced diffuse radiation to determine the light absorption of the particle using the intensity of the measuring light beam and the cross-sectional area of the particle illuminated by the measuring light beam.

The electrode arrangement may be of any desired construction so long as it allows positioning of an electrically charged particle. Hence, it would be sufficient, for example, if the electrode arrangement has two ring electrodes.

However, it is even more advantageous if the electrode arrangement has two ring electrodes for generation of a d.c. electric field, two ring electrodes for generation of an a.c. electric field, since a higher degree of stability of the particle may be achieved on positioning with this solution.

It is particularly expedient if the electrodes for the alternating current field and the direct current field are arranged separately from one another.

The a.c. field electrodes are preferably arranged between the d.c. field electrodes, as a result of which the particles may be better stabilised.

It is even more advantageous for stabilisation of the particle if the a.c. field electrodes have a larger diameter than the d.c. field electrodes.

An Ulbricht sphere in the sense of this invention is formed by a spherical inside surface of a spherical housing which is provided with a coating diffusely reflecting the measuring light.

This coating is a white diffusely reflecting coating, for example, in the case of visible light, and a gold coating, for example, in the case of infrared light.

Moreover, it is preferably provided that the electrodes of the electrode arrangement are provided with the same diffusely reflecting coating as the Ulbricht sphere.

Moreover, it is also provided that the sensor is fitted with a screening shutter shielding against measuring light reflected directly by the particle to ensure that the sensor only measures the intensity of the light diffusely reflected in the Ulbricht sphere.

The sensor may be constructed in a wide variety of ways. However, it must be suitable for measuring the intensity of the measuring light. Hence, a photo-multiplier or a photo-diode may be used, for example, when measuring light in the visible range is used, whereas infrared-sensitive diodes are used, for example, in the infrared range.

Moreover, to provide the possibility of having the measuring light beam to pass through the Ulbricht sphere, in particular for determination of the illuminated cross-sectional area of the particle, the Ulbricht sphere is preferably provided with a closable exit port located opposite the entrance port for the measuring beam.

This exit port may be closed for measurement of the intensity of the radiation diffusely reflected in the Ulbricht sphere, whereas the exit port is open for determination of the cross-sectional area of the particle illuminated by the measuring light beam.

To simplify the determination of the cross-sectional area of the particle illuminated by the measuring light beam, it is preferably provided that the measuring light beam exiting from the exit port may be projected onto a projection surface by means of an optical projection unit.

In this case, the dimensions of the optical projection unit are preferably such that the particle positioned contact-free in the electrode arrangement may be projected as a magnified image onto the projection surface by this unit. A magnification to several times, e.g. ten times, natural size is preferably worked with.

The projection surface may itself be formed by the surface of a photosensitive element, for example. Such a photosensitive element could be a photographic film, for example. However, it is particularly advantageous if the projection surface is formed by a photosensitive surface of an electronic camera, since this facilitates evaluation of the imaging, in particular of the shadow outline of the particle projected onto the projection surface.

No further details have thus far been given in conjunction with the explanation of the preceding embodiments with respect to the measuring light beam used. Visible light in the spectral range of between about 200 nm and about 800 nm, for example, is used as measuring light.

However, it is also possible to use infrared light where the absorption of the particle is to be determined in the infrared range.

Moreover, a lamp may be used as measuring light source. However, because of the advantageous imaging properties of laser beams, it is more advantageous to use a laser as measuring light source which preferably operates in a wavelength in the visible light range. In the simplest case, a helium-neon laser is used for this purpose, which moreover has the advantage of having an essentially constant intensity profile over its beam cross-section.

Further features and advantages of the invention are the subject of the following description as well as of the drawing of some examples.

DETAILED DESCRIPTION OF THE INVENTION

Figure 1:
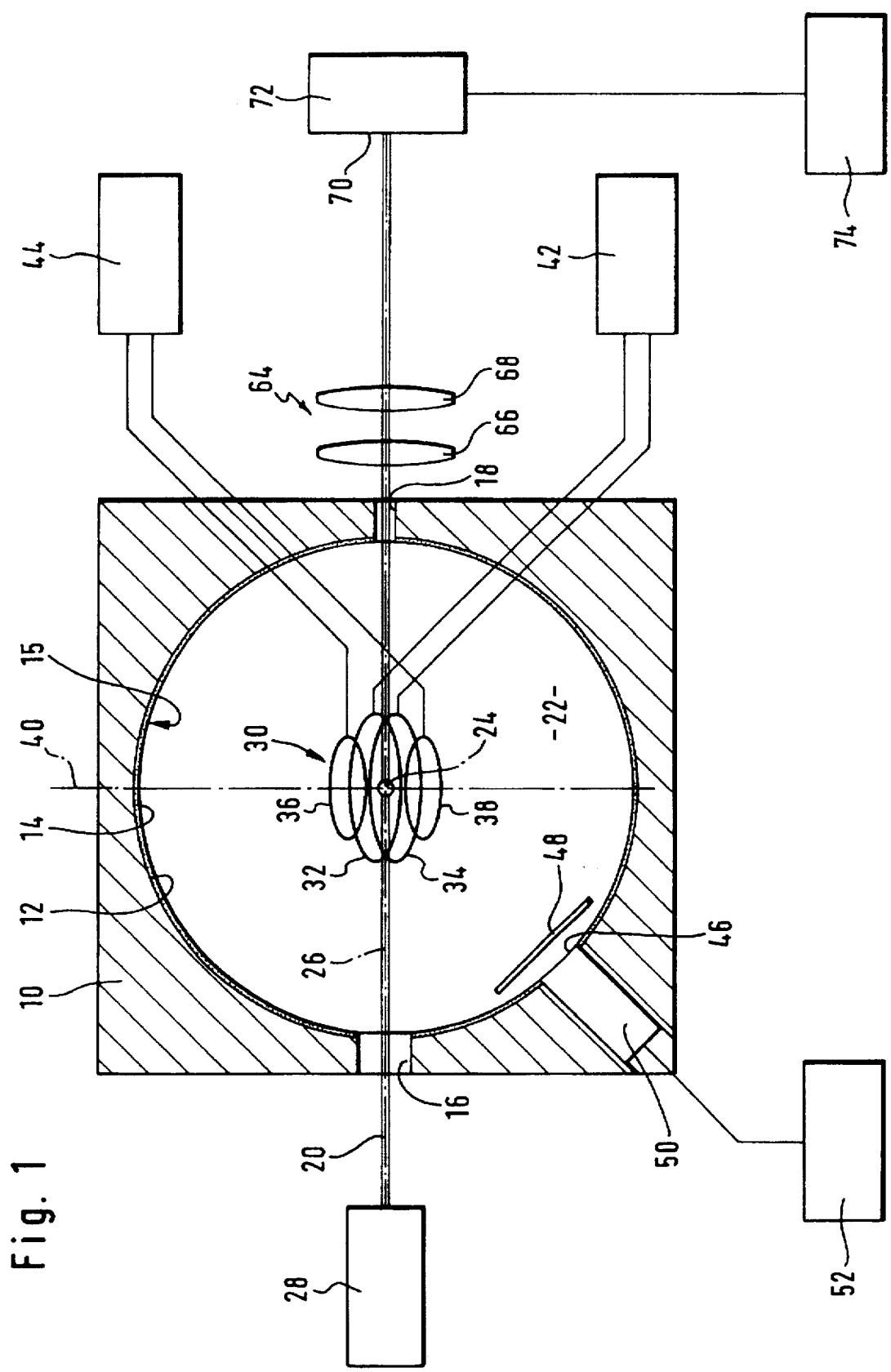
FIG. 1 a schematic representation of a device according to the invention with cut-away Ulbricht sphere.

An example shown in FIG. 1 of a device for measurement of the absorption of particles of random form comprises a spherical housing given the overall reference 10, which has an inner spherical surface 12, which is provided with a diffusely reflecting coating 14 for formation of a diffusely reflecting Ulbricht sphere 15. In this case, the diffusely reflecting coating 14 consists of a white, diffusely reflecting paint, for example, in the case where the absorption of particles of random form is to be measured by visible light, or consists of a gold coating, for example, in the case where longer-wave light, e.g. infrared light, is used as light.

The diameter of the spherical surface 12 amounts to about 120 mm.

The spherical housing 10 also comprises an entrance port 16 and an exit port 18 which are arranged so that a measuring light beam 20 can enter an inside area 22 of the Ulbricht sphere 15 enclosed by the spherical surface 12 through the entrance port 16, pass through this inside area parallel to a straight line 26 passing through a centre point 24 of the Ulbricht sphere 15 and exit again through the exit port 18.

The exit port 18 preferably has a diameter corresponding to double the diameter of the measuring light beam 20.

In this case, the measuring light beam 20 is preferably a laser beam generated by a laser head 28.

Symmetrical to the straight line 26 and to the centre point 24 of the Ulbricht sphere 14, an electrode arrangement 30 is provided in the inside area 22 which comprises two a.c. field electrodes 32, 34 arranged symmetrically to the straight line 26 and to the centre point 24, and two d.c. field electrodes 36, 38 likewise arranged symmetrically to the straight line 26 and to the centre point 24. In this case, electrodes 32 to 38 are constructed in the form of circular rings which are all arranged coaxially to an electrode axis 40, said two circular rings of the a.c. field electrodes 32, 34 lying between the circular rings of the d.c. field electrodes 36, 38, and moreover the circular rings of the a.c. field electrodes 32, 34 having a diameter approximately double the diameter of the rings of the d.c. field electrodes 36, 38.

The two a.c. field electrodes 32, 34 are connected in this case to an a.c. voltage generator 42, whereas the two d.c. field electrodes 36, 38 are connected to a d.c. voltage generator 44.

The voltage difference between the two d.c. field electrodes 36, 38 here lies in a range in the order of 400 volts, whereas the a.c. voltage lies in a range of about 3500 to about 4500 volts, the frequency of the a.c. voltage being in the order of 50 Hz.

The superposition of the a.c. field generated by the a.c. field electrodes 32, 34 and of the d.c. field generated by the d.c. field electrodes 36, 38 results in a minimum potential for an electrostatically charged particle in the centre of the electrode arrangement 30, preferably close to the centre point 24 of the spherical area 12, in which case the particle size preferably lies between about 0.1 μm to about 500 μm. Such a particle can be held in the minimum potential formed by the a.c. field and the d.c. field, in which case the d.c. field preferably runs approximately parallel to the direction of gravitation.

An exact description of the holding of a charged particle in the minimum potential and a calculation of the field may be seen from the article by Davies et al: "The double ring electrodynamic balance for microparticle characterization", Rev. Sci. Instruments, April 1990.

To further ensure that the diffuse radiation in the inside area 22 of the Ulbricht sphere 15 is not influenced at all by the electrode arrangement 30, both the a.c. field electrodes 32, 34 and the d.c. field electrodes 36, 38 are provided with the same diffusely reflecting coating 14 as the spherical area 12 for forming the Ulbricht sphere 15.

The spherical area 22 is moreover also provided with a sensor opening 46, which is located to the side of the straight line 26 and is shielded against the direct entry of light reflected in the region of the centre point 24 by a screening shutter 48, so that only diffusely reflected radiation can enter the sensor opening 46 and strike a sensor 50 to detect its intensity.

This sensor 50 is in turn connected to a measured data logging unit 52.

The measuring light beam 20 exits from the spherical housing 10 through the exit port 18 and enters an optical imaging unit given the overall reference 64, which has two lenses 66, 68, for example, which are adjusted so that a particle arranged in the centre point 24 is magnified and projected onto a projection surface 70, which in the present case is formed by a photosensitive surface of a CCD camera given the overall reference 72, and this camera combined with an evaluation unit 74 permits determination of a shadow outline of a particle positioned in the centre point 24 in a manner still to be described.

For measurement of the albedo of a particle, a plurality of particles are charged by charge transfer, for example, through a rod electrostatically charged by means of friction, in which case the particles then adhere to the rod.

By inserting the rod into the electrode arrangement 30 and lightly tapping it, some charged particles are detached from the rod and are then held in suspension by the electric field of the electrode arrangement 30.

The plurality of particles can be reduced by varying the a.c. voltage for the a.c. field electrodes 32, 34 until only one particle is left in the electric field of the electrode arrangement 30.

This single particle 80 can now be defined by variation of the fields in the electrode arrangement along the electrode axis 40 and be fixed in a stationary manner by corresponding adjustment of the electric fields of the electrode arrangement 30.

Figure 2:
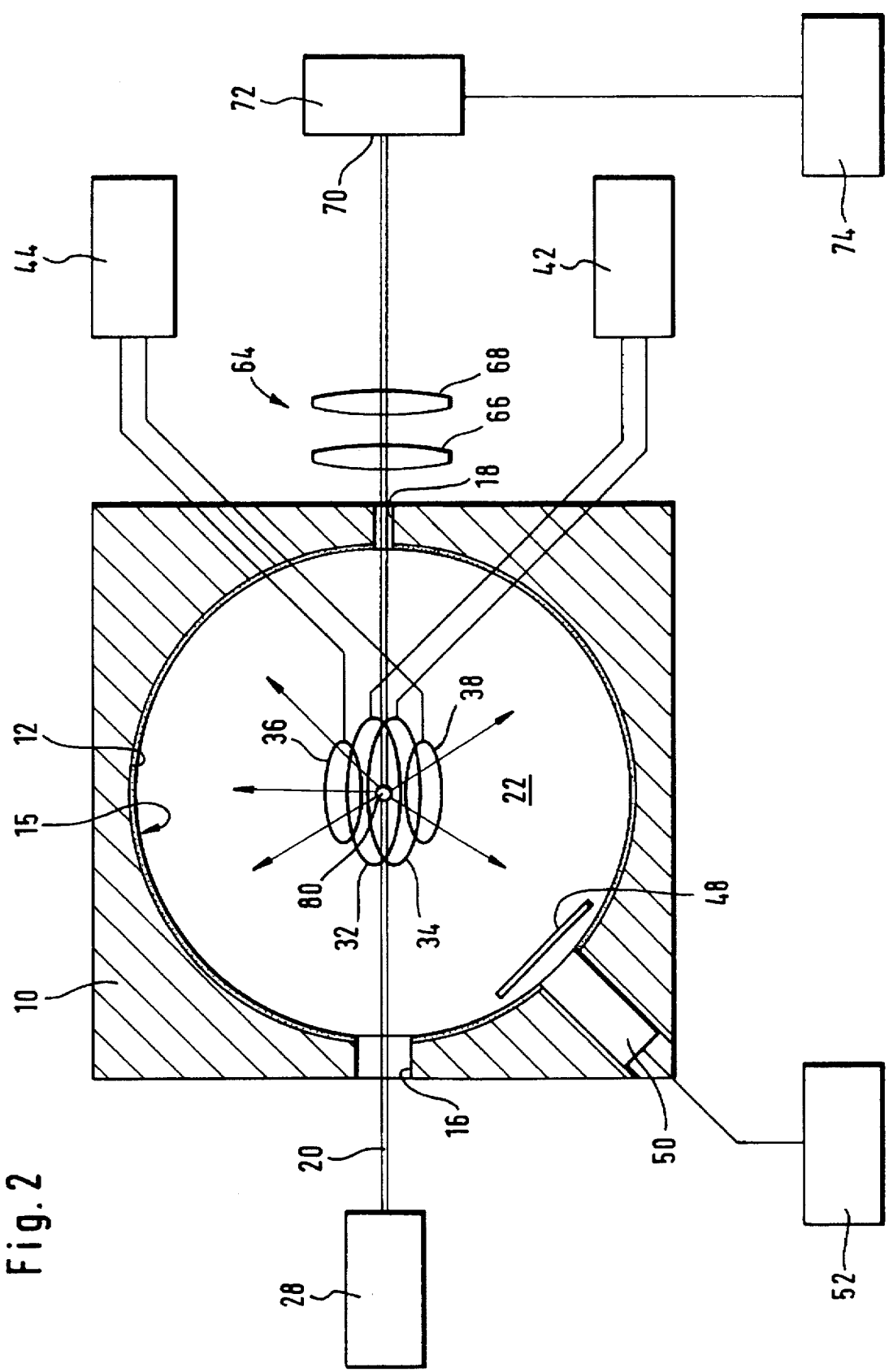
FIG. 2 a schematic representation of the measurement of the absorption and control of measuring light through the particle, and a schematic representation of a measurement of the illuminated cross-sectional area of the particle, and FIG. 3 a schematic representation of a shadow outline of the particle projected onto a projection surface for determination of the cross-sectional area of the particle illuminated by the measuring light beam.

For measurement of the intensity of the radiation of the measuring light beam scattered only on the respective particle 80, the single particle 80 is now positioned, as shown in FIG. 2, within the beam cross-section of the measuring light beam 20 which has a diameter of about 1 mm, for example, said particle 80 having a size of between about 0.1 µm and about 500 µm, as already stated.

The single particle 80, which is preferably positioned close to the centre point 24 of the Ulbricht sphere 15, absorbs and reflects only the measuring light of the measuring light beam 20 striking against this, and the portion of the measuring light beam 20 not striking against the particle 80 leaves the Ulbricht sphere 15 through the exit port 18.

When the particle 80 absorbs measuring light and emits it again, the diffusely reflecting radiation in the inside area 22 of the Ulbricht sphere 15 has a specific solely particle-based intensity I which is detected by the measured data logging unit 52.

Figure 3:
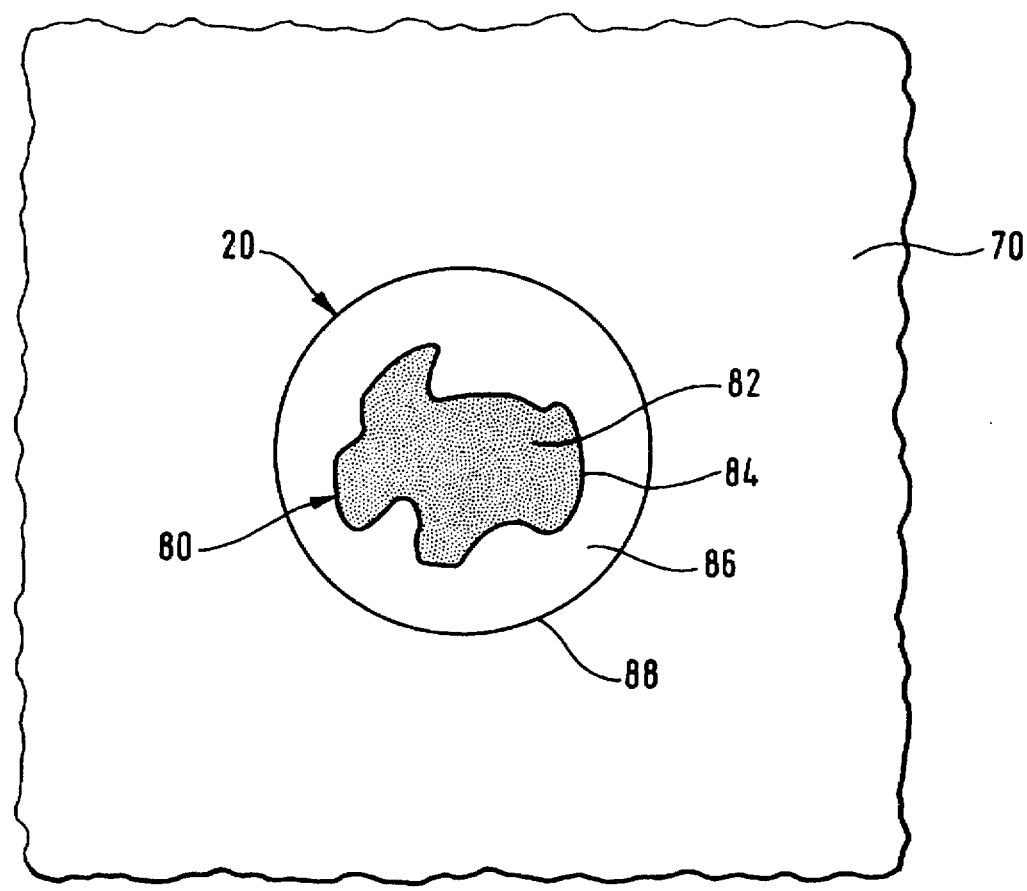

For detecting the exact position of the particle 80 in the measuring light beam 20 and for detecting the cross-sectional area of the particle 80 illuminated by the measuring light beam, the portion of the measuring light beam 20 exiting through the exit port 18 is analysed, in which case the optical imaging unit 64 projects the shadow outline of the particle 80 contained in the measuring light beam 20 onto the projection surface 70 so that, as shown in FIG. 3, an inner shaded region 82 is visible on the projection surface 70 which extends as far as a shadow outline 84 and an illuminated region 86 is recognisable outside the shadow outline 84 which extends as far as an outer boundary line 88, which corresponds to the outer boundary of the beam cross-section of the measuring light beam 20 and allows determination of the cross-sectional area of the beam.

In this case, the single particle 80 is preferably constantly positioned so that the illuminated region 86 still completely surrounds the particle 80, which means that the particle 80 is illuminated by the measuring light beam 20 over its entire particle cross-sectional area running perpendicular to the direction of propagation of the measuring light beam 20.

The particle cross-sectional area of the particle 80 illuminated in a plane perpendicular to the direction of propagation of the measuring light beam 20 can be easily calculated from the shadow outline 84 occurring on the projection surface 70 preferably detected by means of the CCD camera and the evaluation unit 74.

A further decisive factor for calculation of the albedo of the particle 80 is the construction of the intensity distribution within the outer boundary line 88 of the measuring light beam 20. This can be determined with a standard measuring device used for laser beams. In the simplest case, a laser beam is used which has an essentially Gaussian intensity distribution within the outer boundary line 88. With a relatively small diameter of the particle 80 compared to the beam diameter it is not necessary for the relative position of the shadow outline 84 to the outer boundary line 88 to be additionally taken into account in the calculation of the albedo.

Two measurements are carried out for determination of the albedo, namely a measurement on a reference particle 80R and a measurement on the particle 80 of interest.

A particle 80R of a non-absorbent material is preferably used as the reference particle, and then the intensity $I_R$ of the solely reference particle-based diffusely reflected radiation is measured in the inside area 22 of the Ulbricht sphere 15.

In the simplest case, the diameter is known for the reference particle 80R, and therefore this does not have to be determined. However, the above-described method of determining the diameter can be calibrated in this case.

If the diameter of the reference particle is not known, then it is determined as described by projection onto the projection surface 70.

In this case, the measured intensity $I_R$ corresponds to $$I_R = W_R \int_{-R_R}^{R_R} I(r)dr$$

wherein $I_R$: intensity of the particle-based diffusely scattered measuring light, $W_R$: albedo of the reference particle 80R, $R_R$: radius of the reference particle 80R, $I(r)$: radius-dependent intensity distribution in the measuring light beam 20.

The following results in the case of a Gaussian profile of the measuring light beam 20

$$I_R = W_R I_L (1 e^{-2D^2_R/D^2_L})$$

wherein $D_R$: diameter of the reference particle 80R $D_L$: diameter of the measuring light beam 20

$I_L$: maximum intensity of the measuring light beam 20.

Measurement of the intensity $I_R$ of the diffusely reflected, solely particle-based radiation and determination of the diameter D in the particle 80 of interest are also achieved in the described manner.

In this case the measured intensity $I_P$ corresponds to $$I_P = W_P \int_{-R_P}^{R_P} I(r)dr$$

wherein $I_p$: intensity of the particle-based diffusely scattered measuring light, $W_p$: albedo of the particle 80

$R_p$: radius of the particle 80

$I(r)$: radius-dependent intensity distribution in the measuring light beam 20.

The following results in the case of a Gaussian profile of the measuring light beam $$I_R = W_P I_L (1 e^{-2d^2 r^2 / D_L^2})$$

wherein $D_P$: diameter of the particle 80

$D_L$: diameter of the measuring light beam 20

$I_L$: maximum intensity of the measuring light.

If a ratio is formed from the measured intensity $I_R$ and $I_P$ in the case of a Gaussian profile with the same maximum intensity of the measuring light beam 20, then the following results $$\frac{W_P}{W_R} = \frac{I_P(1 - e^{-2D_R^2/D_L^2})}{I_R(1 - e^{-2D_P^2/D_L^2})}$$

and transformed:

$$W_P = \frac{I_P(1 - e^{-2D_R^2/D_L^2})}{I_R(1 - e^{-2D_P^2/D_L^2})} W_R$$

and therefore the albedo $W_P$ of the particle 80 may be determined directly by this.

What is claimed is:

1. A method for determination of the albedo of a particle of random form, wherein:

the particle of random form is electrostatically charged and is positioned contact-free in an Ulbricht sphere by means of an electric field;

the particle of random form thus positioned is illuminated with a measuring light beam passing through the Ulbricht sphere with defined intensity, defined beam cross-section and defined intensity distribution;

an intensity of a solely particle-based diffuse radiation in the Ulbricht sphere is measured by means of a sensor;

a cross-sectional area of the particle of random form illuminated by the measuring light beam is determined;

intensity of a solely reference particle-based diffuse radiation is measured by means of a sensor using a reference particle with known albedo which is electrostatically charged and positioned contact-free in the Ulbricht sphere by means of an electric field, and illuminated with a measuring light beam passing through the Ulbricht sphere with defined intensity, defined beam cross-section and defined intensity distribution; and the albedo of the particle of random form is determined from a ratio of the intensities of the particle-based and reference particle-based diffuse radiation taking into account the cross-sectional area of the particle of random form illuminated by the measuring light beam and the cross-sectional area of the reference particle.

2. A method according to claim 1, wherein:

the particle of random form and the reference particle are each positioned contact-free respectively by means of a d.c. electric and an a.c. electric field.

3. A method according to claim 1, wherein:

the intensity of the measuring light beam is determined after transillumination of the Ulbricht sphere without the particle of random form being illuminated.

4. A method according to claim 3, wherein:

the particle of random form is positioned next to the measuring light beam for determination of the intensity of the measuring light beam.

5. A method according to claim 3, wherein:

a relative position of the measuring light beam and the Ulbricht sphere to one another remain unchanged for determination of the intensity of the particle-based diffuse radiation in the Ulbricht sphere.

6. A method according to claim 1, wherein:

the intensity distribution is determined over the cross-sectional area of the measuring light beam.

7. A method according to claim 1, herein:

the measuring light beam has an essentially Gaussian intensity distribution over its cross-sectional area.

8. A method according to claim 1, wherein:

the cross-sectional area of the particle of random form which is illuminated by the measuring light beam is determined by projection of a shadow outline of the particle of random form positioned in the measuring light beam in the direction of propagation of the measuring light beam onto a projection surface.

9. A method according to claim 8 characterised in that wherein:

the projection surface is arranged outside the Ulbricht sphere.

10. A method according to claim 9, wherein:

the shadow outline of the particle is projected on the projection surface as an image magnified by an optical projection unit.

11. A method according to claim 9, wherein:

the projection surface is formed by a surface of a photosensitive storage element.

12. A method according to claim 11, wherein:

the projection surface is formed by a surface of an electronic image logging unit.

13. A method according to claim 8, wherein:

for measurement of the cross-sectional area of the particle of random form illuminated by the measuring light beam, the measuring light beam and the particle of random form stand in the same relative position to one another as during measurement of the intensity of the diffuse particle-based radiation in the Ulbricht sphere.

14. A method according to claim 1, wherein:

for measurement of the intensity of the diffuse radiation in the Ulbricht sphere with the illuminated particle of random form, substantially the entirety of the particle of random form is positioned within the beam cross-section of the measuring light beam.

15. A method according to claim 1, wherein:

determination of the cross-sectional area of the reference particle is achieved by projecting a shadow outline of the reference particle positioned in the measuring light beam in the direction of propagation of the measuring light beam onto a projection surface.

16. A method according to claim 1, wherein:

the illuminated cross-sectional areas of the reference particle and the particle of random form are substantially the same.

17. A method according to claim 1, wherein: the particle and the reference particle are positioned in the same cross-sectional region of the measuring light beam.

18. A device for determination of the albedo of a particle of random form, comprising:
- an electrode arrangement for the contact-free positioning of said particle, said particle being electrostatically charged wherein:
  - the electrode arrangement is surrounded by an Ulbricht sphere;
  - the Ulbricht sphere is operatively associated with a sensor for measurement of a diffusely reflected radiation in the Ulbricht sphere; and
  - the Ulbricht sphere has an entrance port and an exit port for a measuring light beam for illumination of the particle held contact-free by the electrode arrangement.

19. A device according to claim 18, wherein:
the electrode arrangement as two d.c. field electrodes for generation of a d.c. electric field; and
the electrode arrangement has two a.c. field electrodes for generation of an a.c. electric field.

20. A device according to claim 19, wherein:
the electrodes for the alternating current field are arranged separately from one another in said Ulbricht sphere; and
the electrodes for the direct current field are arranged separately from one another in said Ulbricht sphere.

21. A device according to claim 20, wherein:
the a.c. field electrodes lie between the d.c. field electrodes.

22. A device according to claim 20, wherein:
the a.c. field electrodes have a larger diameter than the d.c. field electrodes.

23. A device according to claim 18, wherein:
the electrodes of the electrode arrangement and the Ulbricht sphere are provided with the same diffusely reflecting coating.

24. A device according to claim 18, wherein:
the sensor is provided with a shutter to shield against measuring light reflected directly by the particle.

25. A device according to claim 18, wherein:
the Ulbricht sphere is provided with a closable exit port located opposite the entrance port for the measuring beam.

26. A device according to claim 25, wherein:
the measuring light beam exiting from the exit port may be projected onto a projection surface by means of an optical projection unit.

27. A device according to claim 26, wherein:
the projection surface is formed by the surface of a photosensitive element.

* * * * *